United States Patent [19]

Fleck et al.

[11] Patent Number: 4,526,976
[45] Date of Patent: Jul. 2, 1985

[54] THIENO[3,2-B]BENZOFURAN AND BENZOTHIOPHENE DERIVATIVES USEFUL AS OPTICAL BRIGHTENING AGENTS

[75] Inventors: Fritz Fleck, Bottmingen, Switzerland; Alec V. Mercer, Bramhope; Malcolm Oates, Cleckheaton, both of England

[73] Assignee: Sandoz Ltd., Basel, Switzerland

[21] Appl. No.: 480,221

[22] Filed: Mar. 30, 1983

[30] Foreign Application Priority Data

Apr. 6, 1982 [GB] United Kingdom ............... 8210225

[51] Int. Cl.³ ........................................... C07D 495/04
[52] U.S. Cl. .................................... 548/159; 548/217; 548/220; 548/327; 252/301.27; 252/301.28
[58] Field of Search ............... 548/159, 217, 327, 220

[56] References Cited

U.S. PATENT DOCUMENTS 4,022,781  5/1977  Narayanan ........................ 548/217

FOREIGN PATENT DOCUMENTS 42536    12/1981  European Pat. Off. ............ 548/217
1959809   4/1971  Fed. Rep. of Germany ...... 548/217
2733439   2/1978  Fed. Rep. of Germany ...... 548/159

Primary Examiner—Robert Gerstl
Attorney, Agent, or Firm—Gerald D. Sharkin; Richard E. Vila; Thomas C. Doyle

[57] ABSTRACT

Compounds of formula I

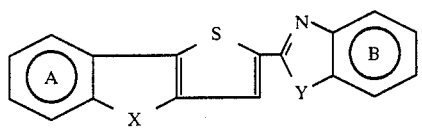

in which
X is O or S;
Y is O, S or $NR_3$ where $R_3$ is hydrogen or $C_{1-4}$alkyl (preferably methyl or ethyl) and rings A and B may be further substituted by non-chromophoric substituents.

10 Claims, No Drawings

THIENO[3,2-B]BENZOFURAN AND BENZOTHIOPHENE DERIVATIVES USEFUL AS OPTICAL BRIGHTENING AGENTS

The invention relates to thieno-containing compounds suitable for use as optical brighteners.

The invention provides compounds of formula I

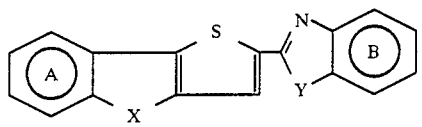

in which
X is O or S;
Y is O, S or $NR_3$ where $R_3$ is hydrogen or $C_{1-4}$alkyl (preferably methyl or ethyl) and rings A and B may be further substituted by non-chromophoric substituents.

Preferred compounds of the invention are of the formula Ia

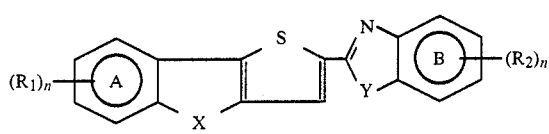

in which X and Y are above defined;
each n independently, is 0, 1, 2 or 3;
each $R_1$ independently and each $R_2$ independently is selected from $C_{1-4}$alkyl; halogen; $C_{1-4}$alkoxy; nitrile; —$CONH_2$; —$COOR_3$ where $R_3$ is defined above; methylsulphony; phenyl unsubstituted or mono-substituted by halogen, $C_{1-4}$alkyl or $C_{1-4}$alkoxy, or when n=2 both $R_1$'s and/or both $R_2$'s are ortho to each other and form a benzo ring fused to ring A or ring B respectively which benzo ring is preferably unsubstituted, but may be mono-substituted by a group $R_{10}$; or when n=1 $R_1$ and/or $R_2$ is the group (a)

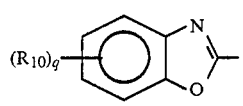

where $R_{10}$ is $C_{1-4}$alkyl or halogen; and q is 0 or 1, preferably 0.

"Halogen" signifies fluorine, chlorine or bromine, preferably chlorine or bromine, more preferably chlorine; any $C_{1-4}$alkoxy present is preferably methoxy and any $C_{1-4}$alkyl present (except when $R_3$) is preferably methyl. Further, where a symbol appears more than once in a formula its significances are independent of one another.

When n=2 and both $R_1$'s form a benzo ring fused to ring A, the benzo ring is preferably attached at the 7,8-position of the moiety.

Preferably n is n' where n' is 0, 1 or 2.

Preferably $R_1$ is $R_1'$ and $R_2$ is $R_2'$ where each $R_1'$ independently and each $R_2'$ independently is selected from $C_{1-4}$alkyl, $C_{1-4}$alkoxy and chlorine or when n=2 both $R_1$'s and/or both $R_2$'s are ortho to each other and form a benzo ring fused to ring A or ring B respectively. More preferably $R_1$ and $R_2$ are $R_1''$ and $R_2''$ where each $R_1''$ and each $R_2''$ independently, is selected from $CH_3$ and Cl.

Preferably X is O.

Preferably Y is Y' where Y' is O or S, more preferably Y' is S.

Preferred compounds of formula Ia are of the formula II

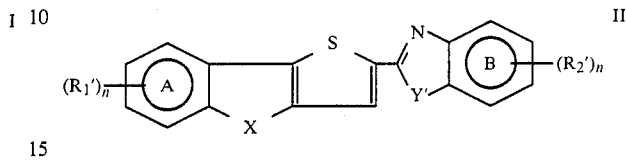

where $R_1'$, n, $R_2'$, Y' and X are as above defined.

More preferred compounds of formula Ia are of the formula III

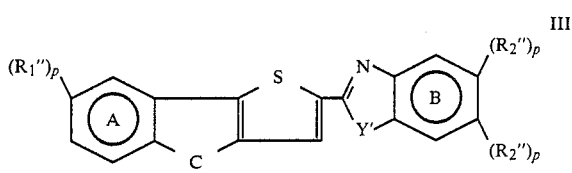

where each p, independently, is 0 or 1, $R_1''$ is methyl or chlorine, each $R_2''$ is methyl and Y' is as defined above.

Most preferred compounds of formula Ia are of the formula IV

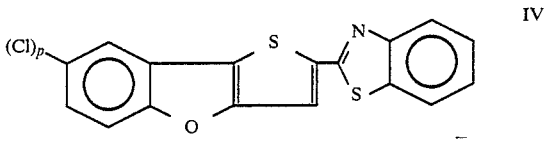

where p is 0 or 1.

The compounds of formula I can be prepared by cyclising compounds of formula VII

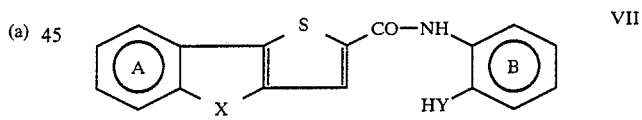

where X, Y and rings A and B are as above defined. Preferably ring A and ring B are not substituted by —$CONH_2$, nitrile or $COOR_3$ groups (as defined above). Preferably cyclisation is achieved by heating in an inert solvent.

The compounds of formula VII are new. Preferred compounds of formula VII are of formula VIIa

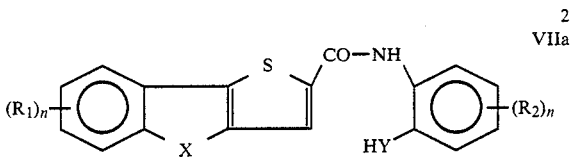

where $R_1$, $R_2$ and n are defined above.

The compounds of formula VII can be prepared by reacting a compound of formula V

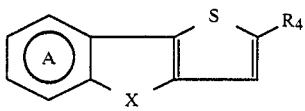

where $R_4$ is carboxyl, carboxylic ester or acyl halide (preferably chloride, bromide or iodide) and ring A and X are above defined, with a compound of formula VI

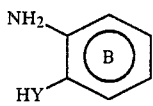

where Y and ring B are above defined (except ring B cannot contain —$CONH_2$, nitrile, or $COOR_3$ groups).

The compounds of formula V are novel and may be prepared from compounds of the formula VIa

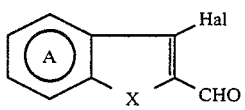

where Hal is halogen, and thioglycollic acid or the $C_{1-4}$alkyl ester of thioglycollic acid under basic conditions.

Preferred compounds of formula V are of formula Va

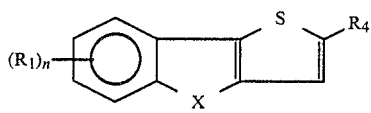

where $R_1$, $R_4$ and n are defined above.

Preferred carboxylic esters of $R_4$ are of the formula

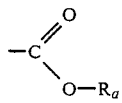

where $R_a$ is $C_{1-4}$alkyl.

Conversion of the acid of formula V to the amide of formula VII can be achieved by conventional methods. For example the acid can be converted to the acid chloride by reaction with thionyl chloride in an inert solvent, for example chloroform, toluene or chlorobenzene at a temperature in the range 40° to 140° C., preferably 50° to 110° C. The acid chloride can then be reacted in the same or a different inert solvent with a compound of formula VI. The amides of formula VII can be isolated by filtration and can be converted to compounds of formula I by heating them in an inert high boiling solvent such as sulpholane, dichlorobenzene or trichlorobenzene for 1 to 24 hours, preferably 2 to 4 hours at temperatures in the range 180° to 240° C., preferably 200° to 240° C. in the presence of an acid catalyst for example boric acid or p-toluene sulphonic acid.

When compounds of formula I are prepared without isolation of amides of formula VII compounds of formula V and of formula VI are heated together either in the absence of a solvent or in the presence of an inert solvent for example sulpholane or trichlorobenzene in the presence of an acid catalyst such as boric acid. The reaction is usually carried out in two stages. In the first stage the reaction mixture is heated at a temperature in the range 80° to 200° C., preferably 120° to 180° C. for ½ to 8 hours, preferably 1 to 4 hours; in the second stage the mixture is heated for a further 1 to 24 hours, preferably 1 to 4 hours at a temperature in the range 100° to 290° C., preferably 130° to 240° C. The products are usually isolated by filtration. This method is unsuitable for the preparation of compounds of formula I where rings A and B are substituted by nitrile, carboxyl or $COOR_3$ groups (as defined above). Alternatively the compounds of formula I can be prepared by interaction of compounds of formula V where $R_4$ is —$CO_2H$ with compounds of formula VI according to the general procedure described be Seha and Weis (Helv. Chim. Acta. 63, 413 [1980]. The esters can be conventionally converted into the acid groups for example by refluxing with aqueous alkali in inert solvent.

The compounds of formula I can be prepared by reacting alkali metal sulphide or hydrosulphide with one of a compound of formula VIII

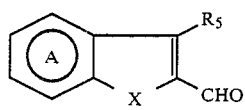

and a compound of formula IX

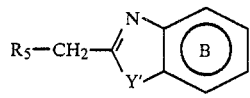

in which ring A, X, and ring B are above defined, and Y' is O or S, $R_5$ is chlorine, bromine or iodine, preferably chlorine or bromine; in the presence of added base, followed by reacting the so-formed sulphide product with the other of the compounds of formula VIII or XI.

Compound IX can also be first reacted with an alkali metal disulphide to form the corresponding disulphide which is then condensed with a compound of formula VIII in the presence of a reducing metal such as sodium or zinc to give a compound of formula I. The reaction is shown below:

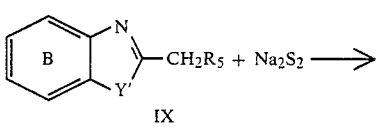

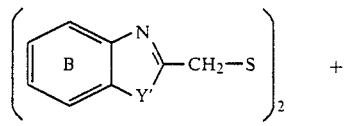

-continued

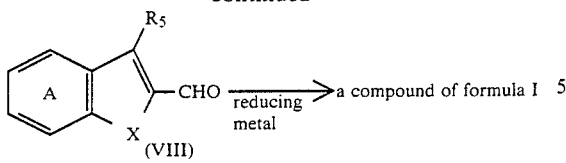

The reactions are normally carried out in two stages in a suitable solvent, for example dimethylformamide, N-methyl pyrrolidone or ethanol. Typically a solution of a compound of formula VIII and a compound of formula IX can be stirred together with an alkali metal sulphide for 1 to 2 hours at 0° to 30° C. Then a tertiary organic base, for example triethylamine is added and the reaction continued for 1 to 6 hours at 80° to 160° C. The product is isolated from the cooled reaction mixture by filtration. Compounds of the formula VI to IX can be prepared according to the known methods from known compounds.

Interconversions can be carried out according to known methods, for example nitriles (where one or more substituent on ring A and/or ring B is —CN) can be prepared by reaction of the corresponding bromide with cuprous cyanide in an inert solvent such as quinoline.

The compounds of formula I are useful as optical brightening agents in particular being suitable for application to polyester by conventional methods such as exhaustion and thermosolling or by spin mass application. The compounds of formula I may be used with or preferably without the need for a carrier in application methods.

The compounds of formula I may be combined with one or more optical brighteners in an optical brightening composition. Such optical brighteners with which the compounds of formula I may be combined are described in DAS No. 1,040,555, French Pat. No. 1,154,529, DOS No. 1,235,255, DOS No. 1,282,021, DOS No. 2,247,791, DAS No. 1,112,072, DOS No. 1,273,479 and Belgian Pat. No. 838,244. Mixtures are preferably in the range 9:1-1:9 of the compounds of formula I to such optical brighteners described in the above patents or published patent applications.

The disclosure of the optical brighteners of these patents or patent applications are incorporated by reference herein.

The invention will now be illustrated by the following Examples in which all temperatures are in degrees Centigrade unless indicated to the contrary.

EXAMPLE 1

A suspension of 15.5 g thieno[3,2-b]benzofuran-2-carboxylic acid, 16.9 g of thionyl chloride, 150 ml of chloroform and 1 ml of dimethylformamide is refluxed 5 hours, the reaction mixture is screened and the solvent removed from the filtrate to yield thieno[3,2-b]benzofuran-2-carboxylic acid chloride as a brown solid. 5.1 g of the above mentioned acid chloride is added portionwise over 30 minutes to a stirred mixture of 2.7 g of 2-aminothiophenol, 50 ml of toluene and 5 ml of pyridine cooled in an ice bath. The mixture is then stirred at ambient temperature for 17 hours, cooled, filtered and the residue washed with ligroin to yield the amide of formula (X)

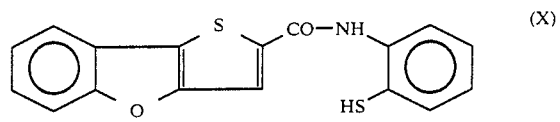

as a brown solid.

A mixture of the amide of formula (X), boric acid and sulpholane is heated under a stream of nitrogen and is brought to a temperature of 230° C. for over 3 hours. The mixture is heated at 230° C. for a further 1 hour, cooled and poured into 60 ml of water. The dark brown solid product is filtered off, washed with water dried and crystallised from cellosolve, chromatographed on a silica gel column and finally recrystallised from chlorobenzene to give the benzthiazole of formula (2) as pale yellow needles m.p. 249°-50° C.;

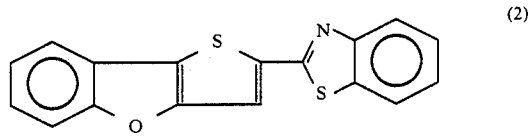

The thieno[3,2-b]benzofuran-2-carboxylic acid used as starting material is prepared as follows:

A mixture of 27.1 g of 3-chloro-2-formyl benzofuran (Chem. Abs. 59 15239b), 19.1 g of methylthioglycollate, 150 ml of pyridine and 18.9 g of water is stirred together and cooled to 15° C. 30 ml of triethylamine is added dropwise to the stirred mixture at 15° C. over 15 minutes. The mixture is then stirred, first at ambient temperature for 1 hour, then at 45° C. for 1 hour and cooled below 20° C. whilst 30 ml of a 50% potassium hydroxide is added dropwise over 15 minutes. The mixture is stirred at ambient temperature for 1 hour, poured into 1500 ml of water and filtered.

The solid product is heated under reflux for 4 hours with a mixture of 6.75 g of potassium hydroxide and 100 ml of alcohol. 25 ml of water is then added, the mixture is refluxed for a further 1 hour and then poured into 250 ml of hot water. The whole mixture is brought to the boil and screened. The resultant filtrate is acidified with hydrochloric acid and the precipitated thieno[3,2-b]benzofuran-2-carboxylic acid is filtered off, washed with water and dried.

EXAMPLES 2-14

Using appropriate starting materials and following the procedure of Example 1 compounds of formula (3) can be prepared.

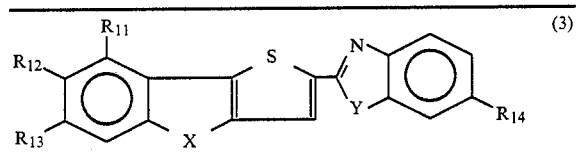

| Example | $R_{11}$ | $R_{12}$ | $R_{13}$ | $R_{14}$ | X | Y | m.p. °C. |
|---|---|---|---|---|---|---|---|
| 2 | H | $CH_3$ | H | H | O | S | 198-9 |
| 3 | H | Cl | H | H | O | S | 222 |
| 4 | H | H | H | —$OCH_3$ | O | O | 187 |
| 5 | H | H | H | H | O | O | 239 |
| 6 | $CH_3$ | Cl | $CH_3$ | H | O | O | 253-5 |
| 7 | $CH_3$ | Cl | $CH_3$ | H | O | S | 237-9 |
| 8 | H | H | H | H | S | S | 200-1 |
| 9 | H | H | H | H | S | O | 207-8 |

-continued

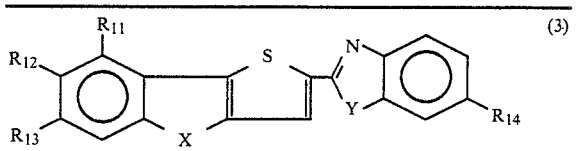

(3)

| Example | $R_{11}$ | $R_{12}$ | $R_{13}$ | $R_{14}$ | X | Y | m.p. °C. |
|---|---|---|---|---|---|---|---|
| 10 | H | H | H | Br | S | O | 196–202 |
| 11 | H | H | H | —OCH$_3$ | S | O | 212 |
| 12 | H | H | Br | H | S | O | 248–58 |
| 13 | H | H | Br | —OCH$_3$ | S | O | 278–85 |
| 14 | H | H | CH$_3$ | H | O | S | 220–22 |

EXAMPLE 15

A mixture of 8 g of 7-methyl thieno[3,2-b]benzofuran-2-carboxylic acid, 4.2 g of 2-amino-5-methyl phenol, 0.5 g of boric acid and 20 ml of sulpholane is stirred gently under a stream of nitrogen, first at 160°–170° C. for 1 hour and then at 230°–40° C. for 3 hours. The reaction mixture is cooled and 50 ml of water is added. The tarry product is chromatographed on alumina then recrystallised from acetone, isopropanol and benzene to yield a product formula (4) as a pale salmon coloured solid m.p. 205°–6° C.;

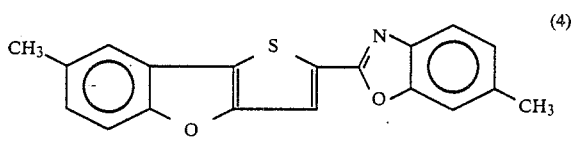

(4)

The 7-methyl thieno[3,2-b]benzofuran-2-carboxylic aicd used as starting material is prepared by a similar procedure to that used for thieno[3,2-b]benzofuran-2-carboxylic acid in Example 1.

EXAMPLES 16–27

Using appropriate starting materials and following a procedure similar to that described in Example 15 compounds of formula (5) can be prepared.

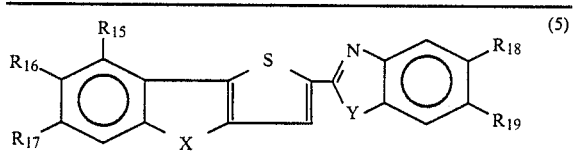

(5)

| Ex. No. | $R_{15}$ | $R_{16}$ | $R_{17}$ | $R_{18}$ | $R_{19}$ | X | Y | m.p. °C. |
|---|---|---|---|---|---|---|---|---|
| 16 | H | H | H | H | CH$_3$ | O | O | 223 |
| 17 | H | CH$_3$ | H | CH$_3$ | H | O | O | 214–5 |
| 18 | H | H | CH$_3$O | H | H | O | O | 196–197 |
| 19 | H | CH$_3$ | H | CH$_3$ | CH$_3$ | O | O | 245 |
| 20 | H | H | H | CH$_3$ | CH$_3$ | O | O | 266 |
| 21 | H | CH$_3$ | H | Cl | H | O | O | 254–55 |
| 22 | (—CH=)$_4$ | | H | H | H | O | O | 241 |
| 23 | H |  | H | H | H | O | O | 228–9 228–9 |
| 24 | H | H | H | H | SO$_2$CH$_3$ | O | S | 315 |
| 25 | H | H | H | H | OCH$_3$ | O | S | 224–6 |
| 26 | H | H | H | H | H | O | NH | 305–6 |

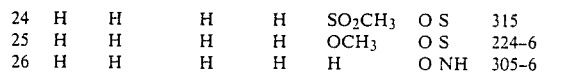

(5)

| Ex. No. | $R_{15}$ | $R_{16}$ | $R_{17}$ | $R_{18}$ | $R_{19}$ | X Y | m.p. °C. |
|---|---|---|---|---|---|---|---|
| 27 | H | H | H | H | H | S NH | 264–5 |

EXAMPLE 28

A mixture of 5 g of thieno[3,2-b]benzofuran carboxylic acid, 30 ml of N-methylpyrrolidone and 3 g of thionyl chloride are mixed together at 0°–10° C. and the mixture stirred for a further 30 minutes at ambient temperature. 3.2 g of 2-aminothiophenol is then added and the temperature of the reaction mixture is brought to 140° C. over 2 hours. The reaction mixture is maintained at 140° C. for a further 2 hours and then cooled. The solid precipitate is filtered off, washed with alcohol and crystallized from xylene to give the compound of Example 1 as pale yellow needles m.p. 248°–9° C.

EXAMPLE 29

A mixture of 6.5 g of 6,7-dimethyl-2-methoxycarbonyl thieno[3,2-b]benzofuran, 3.0 g o-aminophenol and 0.1 g boric acid is heated gradually to 180° C. under a stream of nitrogen. The temperature of the reaction mixture is maintained at 180° C. for a further 30 minutes and then brought to 220°–30° C. The reaction mixture is heated at 220°–30° C. for a further 1½ hr., cooled to 100° C. and 10 ml methanol are added slowly. A brown solid product is collected by filtration and purified by chromatography on a column of alumina followed by crystallization from cellosolve to yield the compound of formula 6 as pale yellow needles m.p. 223°–25° C.

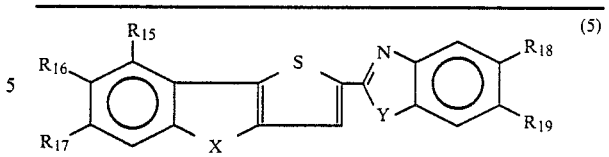

(6)

EXAMPLES 30 AND 31

Using appropriate starting materials and following a procedure similar to that described in Example 29 compounds of formula 7 can be prepared

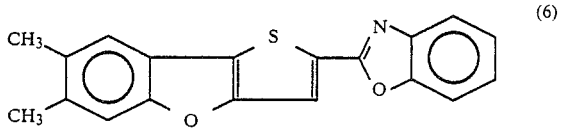

(7)

| Ex. No. | $R_{20}$ | $R_{21}$ | $R_{22}$ | m.p. °C. |
|---|---|---|---|---|
| 30 | CH$_3$ | H | CH$_3$ | 242–44 |
| 31 | H | CH$_3$ | CH$_3$ | 236–39 |

EXAMPLE 32

A solution of 4.1 g of sodium sulphide dihydrate in 200 ml of water is added over 15 minutes to a solution of 6.5 g of 3,5-dichloro-2-formyl benzofuran in 50 ml of dimethylformamide whilst maintaining the temperature of the reaction mixture at 0°-5° C. The mixture is stirred for a further 30 minutes at 0°-5° C. and a solution of 6.6 g 2-chloromethylbenzthiazole (Chem. Abs. 49 13223e) in 80 ml of dimethylformamide is added dropwise at 0°-10° C. over 15 minutes. The mixture is stirred for 1 hour at ambient temperature. 6.1 g of triethylamine is then added, the mixture is stirred at ambient temperature for 30 minutes, then refluxed for 1 hour, cooled and poured into water. The precipitated solid is filtered off, washed well with water, dried and recrystallised from cellosolve to yield the compound of Example 3 as a pale yellow solid.

The 3,5-dichloro-2-formyl benzofuran used as starting material is prepared from 5-chlorocoumaranone by a procedure similar to that used to prepare 3-chloro-2-formyl benzofuran (c.f. Chem. Abs. 59 15239d).

EXAMPLES 33-39

Using appropriate starting materials and following a procedure similar to that described in Example 32 compounds of formula (8) can be prepared

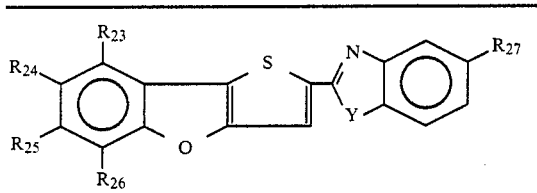

| Ex. No. | $R_{23}$ | $R_{24}$ | $R_{25}$ | $R_{26}$ | $R_{27}$ | Y | m.p. °C. |
|---|---|---|---|---|---|---|---|
| 33 | $CH_3$ | H | $CH_3$ | H | H | S | 195-6 |
| 34 | $CH_3$ | H | $CH_3$ | H | H | O | 213 |
| 35 | H | $CH_3$ | H | $CH_3$ | H | O | 208-9 |
| 36 | H | Cl | H | $CH_3$ | H | S | 214-5 |
| 37 | H | $CH_3$ | H | $CH_3$ | $CH_3$ | O | 178-9 |
| 38 | H | H | H | $CH_3$ | $CH_3$ | O | 199-200 |
| 39 | H | $(CH_3)_3C$ | H | H | H | O | 239 |

EXAMPLE 40

A mixture of 1.85 g of the compound of Example 27 30 ml of dioxan, 1 ml of a 30% solution of sodium hydroxide solution and 3.05 g of dimethyl sulphate is stirred for 3 hours at ambient temperature then at reflux for 2 hours. The reaction mixture is cooled and the precipitated solid is filtered off, washed with ethyl alcohol, dried and recrystallised from isopropanol to give the compound of formula (9) as a pale yellow solid m.p. 247°-51° C.;

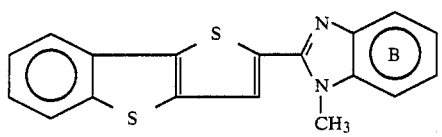

EXAMPLE 41

From the compound of Example 26 and following the procedure of Example 40 a compound of formula (10), m.p. 185°-7° C. can be obtained.

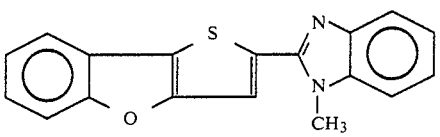

EXAMPLE 42

A mixture of 1.5 g of the compound of Example 12, 0.7 g of cuprous cyanide and 20 ml of quinoline are refluxed 17 hours, cooled and poured into a mixture of 20 ml of concentrated hydrochloric acid and 20 ml of water. The mixture is heated to 70° C. for 30 minutes, cooled and the solid is filtered off washed with water, dried, extracted with hot xylene and finally crystallised from a mixture of dimethylformamide and water and then from butanol to give a compound of formula (11) as a deep yellow solid m.p.>330° C.;

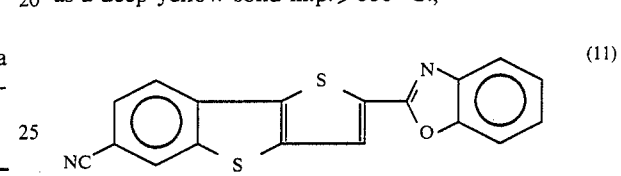

EXAMPLES 43 AND 44

By a similar procedure to that of Example 42 and using the appropriate starting materials, compounds of formula (12) can be prepared.

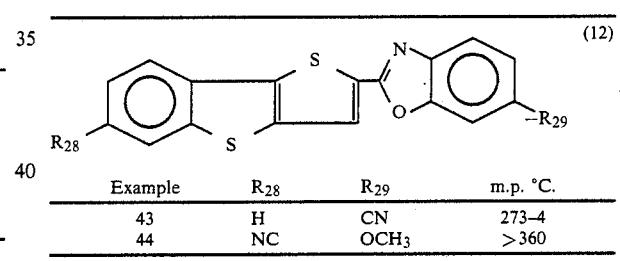

| Example | $R_{28}$ | $R_{29}$ | m.p. °C. |
|---|---|---|---|
| 43 | H | CN | 273-4 |
| 44 | NC | $OCH_3$ | >360 |

EXAMPLE 45

A mixture of 6.6 g of thieno[3,2-b]benzothiophene 2,6-dicarboxylic acid, 150 ml of toluene, 11.9 g of thionyl chloride and 1 ml of dimethylformamide is refluxed for 3 hours, cooled and the precipitate is filtered off, washed with petroleum ether and dried. 6.6 g of the dried solid is added portionwise to a stirred ice cooled mixture of 4.6 g of o-aminophenol, 40 ml of toluene and 16.5 ml of pyridine. The mixture is stirred at ambient temperature for 3 hours and then refluxed 30 minutes. The mixture is cooled, sufficient alcohol is added to granulate the precipitate and the solid diamide is filtered off and dried.

A mixture of 3.7 g of solid diamide, 0,5 g of boric acid and 15 ml of sulpholane is heated under nitrogen. Over 3 hours the reaction temperature reaches 230° C. The reaction mixture is maintained at 230° C. for a further 1 hour, cooled to 90° C., 50 ml of water is added and then the mixture is cooled to ambient temperature, filtered and dried. The crude product is purified by recrystallization from chlorobenzene, nitrobenzene and o-dichlorobenzene to yield the compound of formula (13) m.p. 350° C.

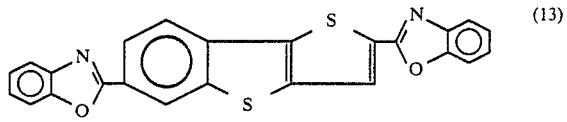

(13)

APPLICATION EXAMPLE A

An 8 g piece of polyester fabric ("Terylene") is padded at 80% expression through 50 ml of an aqueous solution containing 120 mg of the compound described in Example 1 and 75 mg of an ethoxylated ditertiary butylphenol. The compound of Example 1 (of formula 2) is added as a 0.1% dispersion in water containing a sulphonated aliphatic ester and a 10 mole ethylene oxide containing ethoxylated fatty alcohol. The padded piece is thermosolled at 190° C. for 30 seconds. The treated piece shows a brilliant whiteness compared with the untreated fabric.

APPLICATION EXAMPLE B

A 5 g piece of polyester fabric ("Terylene") is immersed at 40° C. in 200 ml of an aqueous mixture containing 50 mg of the compound of Example 15 and 200 mg of a 30 mole ethylene oxide containing ethoxylated castor oil. The compound of Example 15 is added to the bath as a 0.1% aqueous dispersion in a manner analogous to Example A. The fabric is agitated mechanically whilst the temperature of the bath is raised to 95°-98° C. over 30 minutes and then maintained at 95°-98° C. for a further 45 minutes. The fabric is removed from the bath, rinsed thoroughly in water and dried at 80° C. under tension. The treated fabric showed a brilliant whiteness compared to the untreated material.

APPLICATION EXAMPLE C

A 5 g piece of polyester fabric ("Terylene") is agitated at 100° C. for 45 minutes in a closed vessel with 75 ml of an aqueous mixture containing 75 mg of the compound of Example 3 and 75 mg of an emulsified mixture of isomeric tri-chlorinated benzenes. The compound of Example 3 is introduced to the bath as a 0.1% aqueous dispersion (in a manner analogous to Example A). The fabric is removed from the vessel rinsed thoroughly in water and dried at 80° C. under tension. The treated fabric shows a brilliant whiteness compared to the untreated material.

In Application Examples A to C any of the other compounds of Examples 1 to 45 may be used in place of the compound of the named Example.

What we claim is:

1. A compound of formula Ia

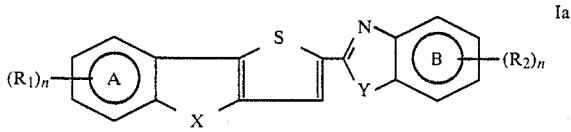

in which
X is O or S;
Y is O, S or $NR_3$,
each n independently is 0, 1, 2 or 3;
each $R_1$, independently, and each $R_2$, independently, is $C_{1-4}$alkyl; halogen; $C_{1-4}$-alkoxy; —$CONH_2$; nitrile; $COOR_3$; methylsulphonyl; or phenyl unsubstituted or monosubstituted by chlorine, $C_{1-4}$alkyl or $C_{1-4}$-alkoxy; or, when n=2, both $R_1$'s and/or both $R_2$'s may be ortho to each other and together form a benzo ring fused to ring A and/or ring B, respectively, which benzo ring is unsubstituted or monosubstituted by a group $R_{10}$; or, when n=1, $R_1$ and/or $R_2$ may be a group (a)

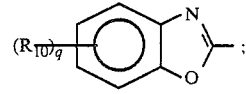

(a)

$R_3$ is hydrogen or $C_{1-4}$alkyl;
$R_{10}$ is $C_{1-4}$alkyl or halogen; and
q is 0 or 1.

2. A compound according to claim 1 wherein each $R_1$, independently, and each $R_2$, independently, as halogen is chlorine or bromine, as alkyl is methyl and as alkoxy is methoxy.

3. A compound according to claim 1 wherein X is O.
4. A compound according to claim 1 wherein Y is Y' where Y' is O or S.
5. A compound according to claim 2 wherein X is O.
6. A compound according to claim 2 wherein Y is Y' where Y' is O or S.
7. A compound according to claim 5 wherein Y is Y' where Y' is O or S.
8. A compound as claimed in claim 1 of the formula II ![Formula II]

in which each $R_1'$, independently and each $R_2'$, independently, is selected from $C_{1-4}$alkyl, $C_{1-4}$alkoxy and chlorine or, when n=2, both $R_1$'s and/or both $R_2$'s may be ortho to each other and together form a benzo ring fused to ring A and/or ring B, respectively, Y' is O or S and each n', independently, is 0, 1 or 2.

9. A compound as claimed in claim 8 of the formula III

![Formula III]

in which
$R_1''$ is methyl or chlorine and each $R_2''$ is methyl, each p independently is 0 or 1; and
Y' is defined in claim 8.

10. A compound as claimed in claim 9 of the formula IV

![Formula IV]

where p is 0 or 1.

* * * * *